(12) United States Patent
Klemm et al.

(10) Patent No.: US 11,666,739 B2
(45) Date of Patent: Jun. 6, 2023

(54) MEDICAMENT DELIVERY DEVICE (71) Applicant: Sanofi, Paris (FR)

(72) Inventors: Thomas Klemm, Frankfurt (DE); Dietmar Hammen, Frankfurt (DE)

(73) Assignee: Sanofi, Paris (FR)

( * ) Notice: Subject to any disclaimer, the term of this patent is extended or adjusted under 35 U.S.C. 154(b) by 1001 days.

(21) Appl. No.: 16/472,263

(22) PCT Filed: Dec. 21, 2017

(86) PCT No.: PCT/EP2017/084146
§ 371 (c)(1),
(2) Date: Jun. 21, 2019

(87) PCT Pub. No.: WO2018/115312
PCT Pub. Date: Jun. 28, 2018

(65) Prior Publication Data
US 2020/0188648 A1 Jun. 18, 2020

(30) Foreign Application Priority Data

Dec. 23, 2016 (EP) .................................... 16206617

(51) Int. Cl.
*A61M 37/00* (2006.01)
*A61N 1/30* (2006.01)

(52) U.S. Cl.
CPC ......... *A61M 37/0015* (2013.01); *A61N 1/306* (2013.01); *A61M 2037/0007* (2013.01); *A61M 2037/0023* (2013.01); *A61M 2205/36* (2013.01)

(58) Field of Classification Search
CPC ...... A61M 37/0015; A61M 2037/0007; A61M 2037/0023; A61M 2205/36; A61N 1/306
USPC .......................................................... 604/501
See application file for complete search history.

(56) References Cited

U.S. PATENT DOCUMENTS

| 2004/0162470 | A1 | 8/2004 | Tu | |
| 2006/0009731 | A1* | 1/2006 | Wu | ....................... A61N 1/0424 |
| | | | | 604/20 |
| 2007/0066934 | A1* | 3/2007 | Etheredge | ......... A61M 37/0015 |
| | | | | 604/173 |
| 2007/0276318 | A1 | 11/2007 | Henley | |
| 2011/0257582 | A1 | 10/2011 | Watanabe et al. | |
| 2014/0066864 | A1* | 3/2014 | Eum | .................... A61B 17/205 |
| | | | | 604/273 |

FOREIGN PATENT DOCUMENTS

| CN | 1608686 | 4/2005 |
| CN | 1610540 | 4/2005 |
| CN | 101262824 | 9/2008 |

(Continued)

OTHER PUBLICATIONS

International Preliminary Report on Patentability in Application No. PCT/EP2017/084146, dated Jun. 25, 2019, 6 pages.

(Continued)

*Primary Examiner* — Phillip A Gray
(74) *Attorney, Agent, or Firm* — Fish & Richardson P.C.

(57) ABSTRACT

The present disclosure relates to a medicament delivery device comprising at least one microneedle for delivering a medicament to a patient, and a system configured to enhance the penetration of the medicament into skin of the patient.

13 Claims, 7 Drawing Sheets

(56) References Cited

FOREIGN PATENT DOCUMENTS

| | | |
|---|---|---|
| CN | 101304782 | 11/2008 |
| CN | 101715354 | 5/2010 |
| CN | 102421480 | 4/2012 |
| CN | 102844072 | 12/2012 |
| CN | 103418081 | 12/2013 |
| CN | 104096311 | 10/2014 |
| CN | 204246683 | 4/2015 |
| CN | 105816952 | 8/2016 |
| CN | 106063971 | 11/2016 |
| EP | 1086719 | 3/2001 |
| JP | 2002-523195 | 7/2002 |
| JP | 2004-505652 | 2/2004 |
| JP | 2008-543872 | 12/2008 |
| JP | 2009-508595 | 3/2009 |
| JP | 2010-253199 | 11/2010 |
| WO | WO 2000/012173 | 3/2000 |
| WO | WO 2000/074767 | 12/2000 |
| WO | WO 02/100459 | 12/2002 |
| WO | WO 2003/024383 | 3/2003 |
| WO | WO 2006/138658 | 12/2006 |
| WO | WO 2007/035710 | 3/2007 |
| WO | WO 2008/114218 | 9/2008 |
| WO | WO 2010/129928 | 11/2010 |

OTHER PUBLICATIONS

International Search Report and Written Opinion in Application No. PCT/EP2017/084146, dated Apr. 24, 2018, 9 pages.

* cited by examiner

MEDICAMENT DELIVERY DEVICE

CROSS REFERENCE TO RELATED APPLICATIONS

The present application is the national stage entry of International Patent Application No. PCT/EP2017/084146, filed on Dec. 21, 2017, and claims priority to Application No. EP 16206617.9, filed on Dec. 23, 2016, the disclosures of which are incorporated herein by reference.

TECHNICAL FIELD

The disclosure relates to a device for delivery of medicament to a patient.

BACKGROUND

A variety of diseases exists that require regular treatment by injection of a medicament. Such injection can be performed by using hypodermic injection devices, which are applied either by medical personnel or by patients themselves. As an example, type-1 and type-2 diabetes can be treated by injection of insulin doses, for example once or several times per day, using an insulin injection device. This type of devices typically comprises a insulin pump connected to cannula or an hypodermic injection needle through which the insulin can flow towards the skin of the patient.

SUMMARY

Some aspects relate to a medicament delivery device.

According to a further aspect, there is provided a medicament delivery device comprising at least one microneedle for delivering a medicament to a patient; and a system configured to enhance the penetration of the medicament into the skin of the patient.

The system may comprise a first electrode, a second electrode, and a power supply connected to the first and second electrodes, the system being configured to generate an electric field between the first and second electrodes, the first and second electrodes being arranged such that, in use, the electric field generated between the first and second electrodes drives the medicament towards the skin of the patient.

The second electrode may be permeable such that, in use, medicament driven by the electric field flows through the second electrode towards the skin of the patient. The second electrode may comprise a perforated plate.

The system may be configured to generate a pulsed electric field between the first and second electrodes.

The system may comprise a heating element configured to heat the skin of the patient.

The heating element may be permeable such that, in use, medicament flows through the heating element towards the skin of the patient. The heating element may comprise a perforated heating foil.

The system may comprise a heat controller for controlling the heating element.

The system may be configured to deliver a chemical penetration enhancer into the skin of the patient.

The system may comprise a mechanism for mixing the chemical penetration enhancer to the medicament prior to the medicament delivery into the skin of the patient.

The medicament delivery device may comprise a porous membrane arranged adjacent to the at least one microneedle, and the porous membrane may be configured to retain the medicament.

The medicament delivery device may comprise a medicament pump mechanism for pumping the medicament towards the at least one microneedle.

The medicament delivery device may comprise a reusable part and a disposable part, and the medicament pump mechanism may be located in the disposable part. In an alternative emboidment, the medicament pump mechanism may be located in the reusable part.

The medicament delivery device may comprise a plurality of microneedles.

The medicament delivery device may comprise a cartridge of medicament.

The medicament delivery device may be an insulin delivery device.

The medicament delivery device may be a wearable device. The medicament delivery device may comprise a a bottom surface configured to removably attach to the skin of the patient.

The medicament delivery device may comprise a controller for controlling the medicament delivery to the patient.

The medicament delivery device may comprise a blood glucose sensor configured to send data relating to the blood glucose of the patient to the controller so that the controller controls the insulin delivery to the patient.

The medicament delivery device may comprise a wireless communication unit configured to transmit and/or receive information to/from another device in a wireless fashion.

According to a further aspect there is provided a method of enhancing the penetration of a medicament into a skin of the patient, comprising using a medicament delivery device comprising at least one microneedle for delivering the medicament to a patient and a system configured to enhance the penetration of the medicament into the skin of the patient.

The system may comprise a first electrode, a second electrode, and a power supply connected to the first and second electrodes, and the method may comprise generating an electric field between the first and second electrodes to drive the medicament towards the skin of the patient.

The system may comprise a heating element and the method may comprise using the heating element to heat the skin of the patient.

The method may comprise delivering a chemical penetration enhancer into the skin of the patient. The method may comprise mixing the chemical penetration enhancer to the medicament prior to the medicament delivery into the skin of the patient.

The method may comprise controlling delivery of the medicament to the patients skin by a controller.

The method may comprise the use of a wireless communication unit provided in the device transmitting and/or receiving information representative of the medicament and/or dose to be administered.

The method may comprise the controller controlling operation of the medicament delivery device dependent on the information received by the wireless communication unit.

The transdermal medicament delivery device may provide a less painful, non-invasive medicament delivery that may be more easily carried out by the patients themselves. The medicament delivery device may also reduce irritation when delivering medicament for long periods of time. Further, the transdermal medicament delivery device may reduce tissue damage and improve transport.

The terms "drug" or "medicament" which are used interchangeably herein, mean a pharmaceutical formulation that includes at least one pharmaceutically active compound.

The term "medicament delivery device" shall be understood to encompass any type of device, system or apparatus designed to immediately dispense a drug to a human or non-human body (veterinary applications are clearly contemplated by the present disclosure). By "immediately dispense" is meant an absence of any necessary intermediate manipulation of the drug by a user between discharge of the drug from the drug delivery device and administration to the human or non-human body. Without limitation, typical examples of drug delivery devices may be found in injection devices, inhalers, and stomach tube feeding systems. Again without limitation, exemplary injection devices may include, e.g. patch devices, autoinjectors, injection pen devices and spinal injection systems.

BRIEF DESCRIPTION OF THE FIGURES

Exemplary embodiments are described with reference to the accompanying drawings, in which.

DETAILED DESCRIPTION

Embodiments provide a medicament delivery device comprising at least one microneedle for delivering a medicament to a patient, and a system configured to enhance the penetration of the medicament into the skin of the patient. Providing such a medicament delivery device may help towards avoiding the use of an injection needle for delivering the medicament to the patient. Since no injection needle is needed, such a medicament delivery device does not require a needle hole to be created at the injection site and so can help towards avoiding tissue injury, as well as helping to reduce pain and discomfort in the medicament delivery process. In addition, irritations and complications that may occur by the introduction and/or presence of a needle into the skin in a conventional needle injection device may be avoided. Furthermore, the system configured to enhance the penetration of the medicament into the skin of the patient may allow the medicament to overcome more easily the skin barrier and to be, therefore, more efficiently administered.

Figure 1:
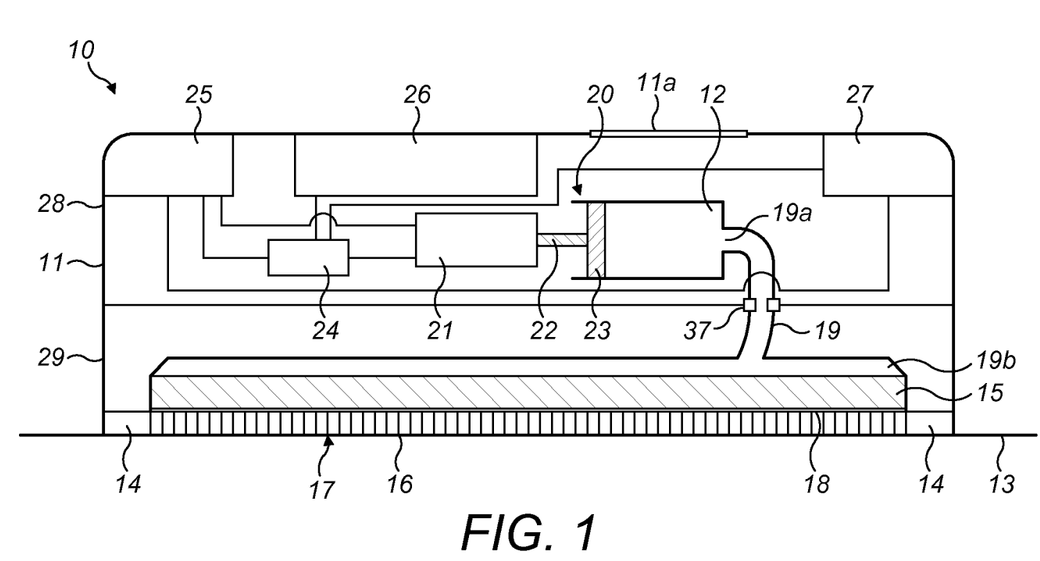
FIG. 1 is a schematic cross-sectional view of a medicament delivery device.

According to some embodiments of the present disclosure, an exemplary drug delivery device 10, herein simply referred to as stem configuris shown in FIG. 1.

In the context of this application, the terms "upstream" and "downstream" are used herein in relation to the direction of medicament flow through the device in normal use. Moreover, the terms "upper", "lower" ower terms devare used herein in relation to the orientation of the device shown in the accompanying drawings.

The drug delivery device, as described herein, may be configured to inject a medicament into a patient. Such a device could be operated by a patient or care-giver, such as a nurse or physician. The device includes a large volume device ("LVD") or patch pump, configured to adhere to a skin of the patient for a period of time (e.g., about 5, 15, 30, 60, 120 minutes or longer) to deliver a "large" volume of medicament (typically about 2 ml to about 10 ml or more).

In combination with a specific medicament, the presently described device may also be customized in order to operate within required specifications. For example, the device may be customized to inject a medicament within a certain time period (e.g. about 10 minutes to about 60 minutes or longer). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP.

The delivery devices described herein can also include one or more automated functions. For example, the medicament injection can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of the present drug delivery device may each be activated via an activation mechanism. Such an activation mechanism can include one or more of a button, a lever or other activation component. Activation of an automated function may be a one-step or multi-step process. That is, a user may need to activate one or more activation components in order to cause the automated function. For example, in a one-step process, a user may depress a button or interact with a user interface in order to cause injection of a medicament. Other devices may require a multi-step activation of an automated function.

Referring to FIG. 1, the device 10 includes a body or housing 11 which typically contains a medicament reservoir 12 (cartridge) pre-filled with liquid medicament to be injected, and the components required to facilitate one or more steps of the delivery process. The device 10 can include a cover or lid 11a which can be removed when the medicament reservoir 12 (cartridge) needs to be changed or refilled. The device 10 can also include a protective cover 13 that can be detachably adhered to a bottom surface of the device 10. Typically, when using the device 10 for the first time, a user must remove the protective cover 13 from the housing 11 before the device 10 can be operated.

The device 10 is intended to be placed on the skin of the patient, e.g. on the abdomen of the patient. The device 10 is preferably a wearable device. Such devices are commonly referred to as "patch pumps" or "skin patches" due to their nature of being worn or affixed to the skin of the patient. The device 10 comprises a device holding element 14 e.g. in the form of an adhesive tape 14 (or pad) configured to adhere to the skin of the patient. The adhesive pad 14 is attached to the bottom side or skin attachement side of the device 10 and covered by the protective cover 13 prior to the first use of the device 10. The adhesive pad 14 ensures the adhesion of the device 10 onto the skin so that in use, the device 10 does not detach from the skin. Alternatively, the device 10 comprises a device holding element operating with vacuum to adhere the device 10 to the skin.

The device 10 includes a medicament receiving element 15 configured to receive the medicament flowing from the medicament reservoir 12. In the embodiment described herein, the medicament receiving element 15 is in the form of a porous membrane, e.g. a fleece or absorbant pad 15. The absorbant pad 15 allows for a substantially continuous controlled delivery of the medicament to the patient.

The device 10 further comprises a microneedle assembly including a plurality of microneedles 16 arranged in an array 17. The microneedle assembly is configured to transdermally deliver medicament to the patient. The array 17 is disposed downstream of the absorbant pad 15, and is configured to deliver to the patient the medicament flowing from the absorbant pad 15. The microneedles 16 extend substantially downwardly from a structure or support 18. The support 18 may be made from a rigid or flexible sheet of metal or plastic. The support 18 is perforated so that medicament can flow through the support 18 towards the microneedles 16. It should be understood that the number of microneedles 16 shown in the figures is for illustrative purposes only. The actual number of microneedles 16 used in the device 10 may, for example, range between around 70 and around 7000 microneedles, depending on the area of the bottom surface of the device 10. The size and shape of the microneedles 16 may also vary as desired. For example, the microneedles 16 may have an overall conical shape, an overall pyramidal shape or a cylindrical portion upon which is positioned a conical portion having a tip. The microneedles 16 are typically of a length sufficient to penetrate the stratum corneum and pass into the epidermis. In certain embodiments, the microneedles 16 have a length ranging between around 0.2 and around 3 millimeters. The microneedles 16 help to overcome the skin barrier by creating pores in the skin, thereby enhancing the penetration of the medicament through the skin. The microneedles 16 perforate the outer skin layer and ensure that the medicament diffuses in the pores thereby created. The uptake of the medicament through the skin works by diffusion, i.e. the medicament flows down a gradient of concentration, from the absorbant pad 15 towards the skin of the patient. Once absorbed, the medicament is transported into the blood e.g. with the lymph. The medicament uptake by the body of the patient via microneedles has been shown to be better than subcutaneously, e.g. via an hypodermic injection needle, in particular in the case of insulin.

The device 10 comprises a tube or hose dispatcher or manifold 19 in fluid communication with the medicament reservoir 12. The manifold 19 includes an inlet 19a connected to the medicament reservoir 12 and a dispense outlet 19b connected to the absorbant pad 15. The manifold 19 is arranged such that, in use, medicament flows from the medicament reservoir 12 through the manifold 19 via the inlet 19a, and towards the absorbant pad 15 via the dispense outlet 19b. The dispense outlet 19b is disposed upstream of the absorbant pad 15 and is configured such that medicament flowing from the manifold 19 is distributed substantially uniformly in the absorbant pad 15. For example, and as visible in FIG. 1, the absorbant pad 15 faces the dispense outlet 19b and the area of the absorbant pad 15 is substantially similar to the area of the cross-section of the dispense outlet 19b.

A pump mechanism 20 is provided to cause the medicament to flow from the medicament reservoir 12 through the manifold 19. The pump mechanism 20 includes a motor 21, a thumb screw 22 and a plug or piston 23. In use, the motor 21 rotates the thumb screw 22, which drives the piston 23 within the medicament reservoir 12 towards the manifold 19. While driven by the motor 21, the piston 23 pushes the medicament out of the reservoir 12 through the manifold 19 via the inlet 19a, and towards the absorbant pad 15 via the dispense outlet 19b. The absorbant pad 15 allows for a uniform distribution of the medicament and therefore ensures that the medicament is homogeneously distributed on on the array 17. The medicament flows from the absorbant pad 15 through the array 17 of microneedles 16, and diffuses through the skin.

The device 10 further comprises a controller 24 for monitoring and/or controlling the operation of the device 10. The controller 24 includes memories such as a Random Access Memory and/or a Read-Only Memory, and a firmware configured to control the motor 21 such that the flow or amount of medicament delivered can be varied, e.g. so that the medicament is pumped at a rate which enables the skin to absorb the medicament. The device 10 also comprises a power supply 25, a user interface 26 and a wireless communication unit 27.

Figure 2:
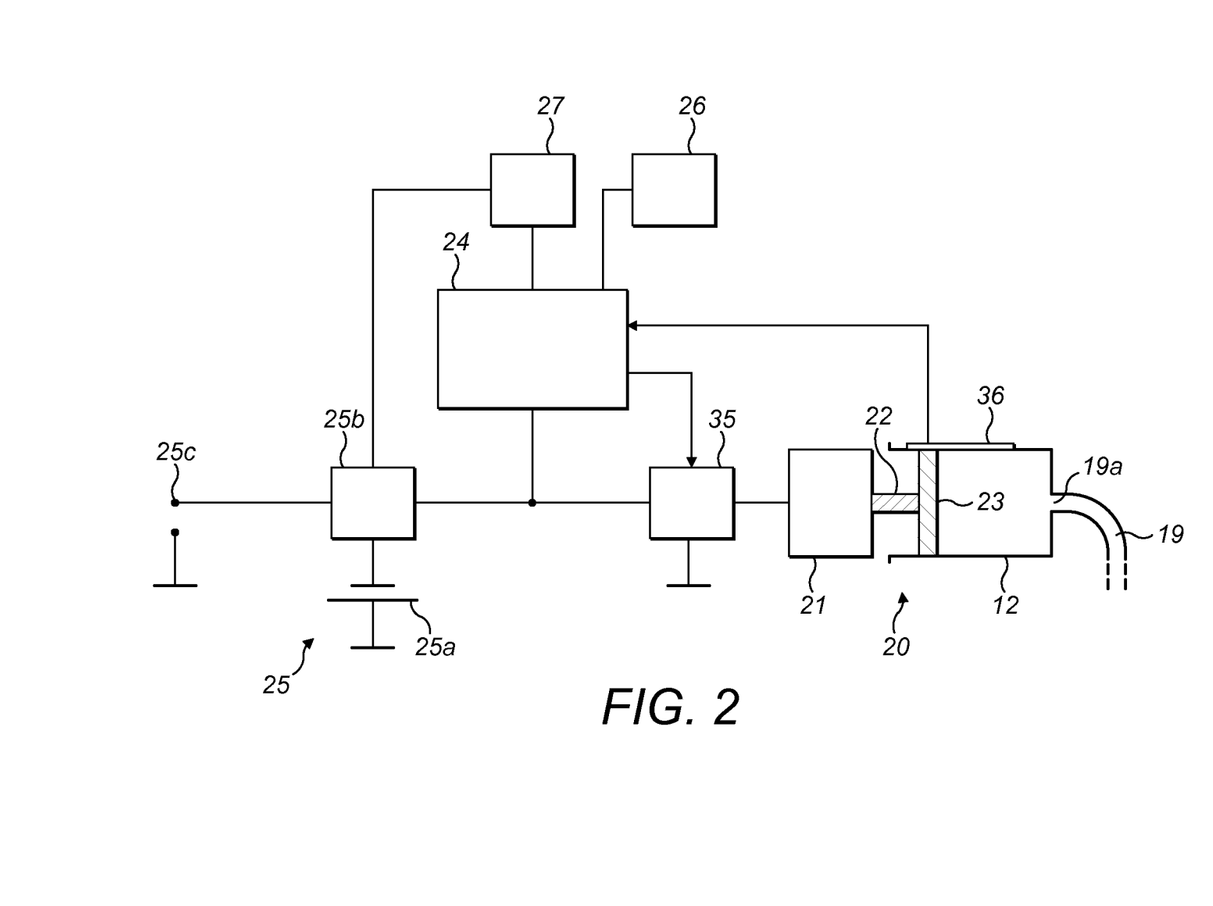
FIG. 2 is a block diagram of a part of the medicament delivery device of FIG. 1.

FIG. 2 is a block diagram schematically showing the electronic components of the device 10 of FIG. 1. The power supply 25 includes a disposable or rechargeable battery 25a, a power controller 25b, and a supply contact 25c. The supply contact 25c is configured to enable the device 10 to be connected to an external power source for powering the device 10 or for recharging the battery 25a. The power supply 25 is connected to the controller 24 and to the wireless communication unit 27 to supply power to each.

The power supply 25 is connected to the motor 21 via a pulse width modulation 35 for powering the motor 21. The controller 24 is connected to the pulse width modulator 35 to control the drive of the motor 21. The controller 24 is also connected to the wireless communication unit 27 and with the user interface 26 to control and receive signal input from each. The pump mechanism 20 and/or reservoir 12 comprise an encoder 36, such as a linear transducer. The encoder 36 is connected to the controller 24 and is configured to send a signal indicative of the position of the piston 23 to the controller 24. Alternatively, or in addition, the encoder 36 is a rotational transducer and is configured to send a signal indicative of the number of rotations of the thumb screw 22 to the controller 24. The controller 24 and the pulse width modulation 35 are powered by the power supply 25.

The wireless communication unit 27 is configured to transmit and/or receive information to/from another device in a wireless fashion. Such transmission may for instance be based on radio transmission or optical transmission. In some embodiments, the wireless communication unit 27 is a Bluetooth transceiver or NFC transceiver. Alternatively, the wireless communication unit 27 may be substituted or complemented by a wired unit configured to transmit and/or receive information to/from another device in a wire-bound fashion, for instance via a cable or fibre connection. When data is transmitted, the units of the data (values) transferred may be explicitly or implicitly defined. For instance, in case of an insulin dose, always International Units (IU) may be used, or otherwise, the used unit may be transferred explicitly, for instance in coded form.

Figure 3:
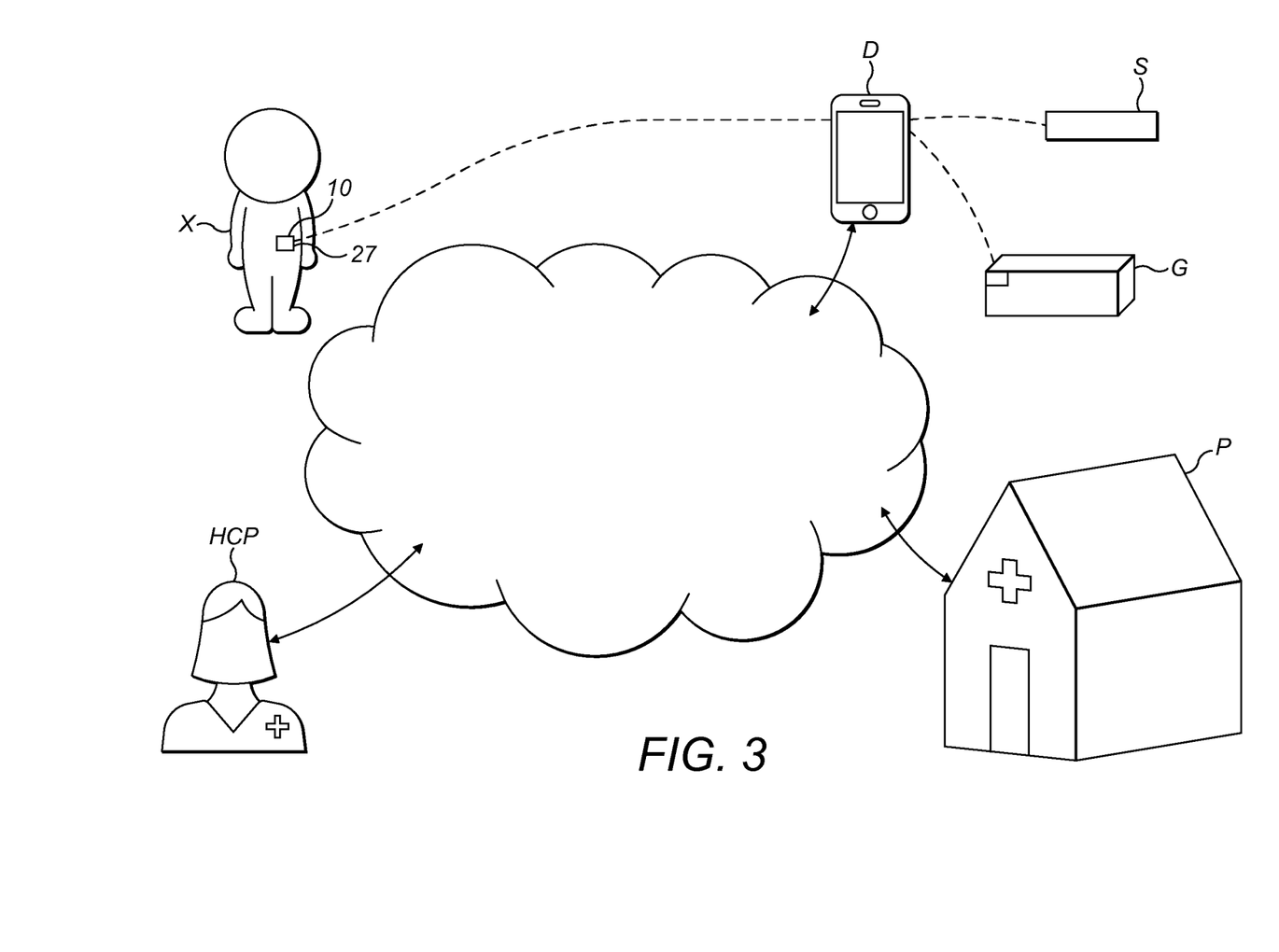
FIG. 3 is a diagram showing a medicament delivery device in wireless connection with various devices.

The controller 24 may be programmed to cause a flow of medicament through the manifold 19 towards the skin of the patient based on instructions from a separate, remote device. As illustrated in FIG. 3, the wireless communication unit 27 may be configured to receive instructions from a remote device D, such as a smartphone or tablet running a specific application. The wireless communication unit 27 is configured to deliver the received instructions to the controller 24. In one embodiment, the remote device D may be in wireless connection with a continuous blood glucose monitoring ("BGM") device G and/or with a test strip-based BGM device S. The test strip-based BGM device S and/or the BGM device G may send data relating to the blood glucose of the patient to the remote device D. The remote device D may then communicate with the controller 24, via the wireless communication unit 27, to control the pump mechanism 20 and thereby the insulin delivery to the patient depending on e.g. the blood glucose level of the patient. For example, a blood glucose sensor as described in US20040162470A1 may be used. Alternatively, the user interface 26 can be used by the patient X or a healthcare professional ("HCP") to directly program the device 10. In addition, the healthcare professional HCP, the patient P or a dispensing pharmacy P may be able to upload data relating to the patient's medicament requirements, to a cloud-based server, and the remote device. D may be able to communicate with the cloud-based server to retrieve such information and control the operation of the device 10 accordingly. For example, a healthcare professional may adjust the medicament regime for a patient X depending on their latest health test or recent BGM results, and upload such data to the cloud-based server. The pharmacy P may be able to upload the specifics of the dispensed medicament to the cloud-based server, such as medicament concentration, advised delivery rate and/or volume.

As shown in FIG. 1, the device 10 comprise an upper or reusable part 28, and a lower or disposable part 29. In use, the reusable part 28 and the disposable part 29 are assembled together. The reusable part 28 may be removably attachable to the disposable part 29, for example when the reusable part 28 is designed to include costly components of the device 10. The reusable part 28 is mechanically connected to the disposable part 29, e.g. the reusable part 28 is clipped to the disposable part 29. The reusable part 28 is further connected to the disposable part 29 at the manifold 19, which connects the medicament reservoir 12 in the reusable part 28 to the absorbant pad 15 in the disposable part 29. In such an embodiment, a fluid coupling 37 may be provided in the manifold 19 to fluidly connect first and second sections of the manifold respectively disposed in the reusable part 28 and disposable part 29 of the device 10. Therefore, when the reusable part 28 and disposable part 29 of the device 10 are mechanically connected together as described above, the fluid coupling makes a fluid tight connection between the first and second sections of the manifold to ensure reliable delivery of the medicament from the reservoir 12 to the absorbant pad 15.

Figure 4:
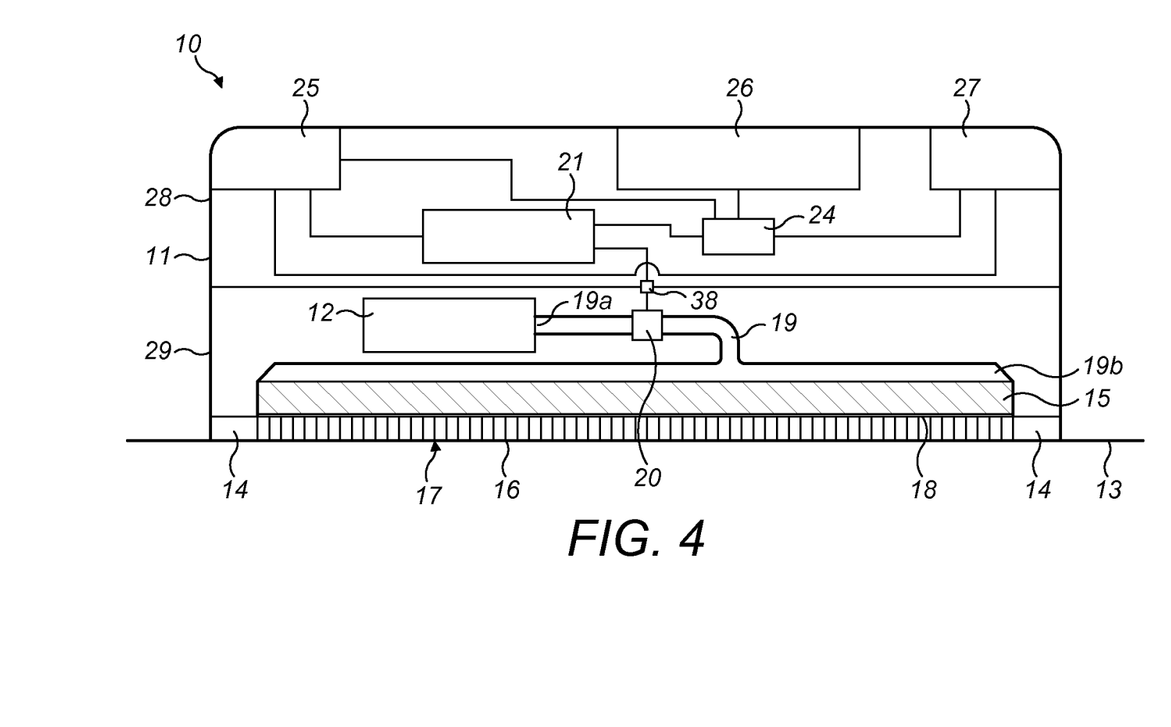
FIG. 4 is a schematic cross-sectional view of a further medicament delivery device.

This arrangement of the device 10 has the advantage that the pump mechanism 20 and the array 17 can be worn together, thereby allowing to avoid the use of a separate supporting device for the pump mechanism 20. This arrangement also allows for a better control of the pump mechanism 20. In the embodiment shown in FIG. 1, the reusable part 28 includes the electronic components of the device 10, the pump mechanism 20 and the medicament reservoir 12. The disposable part 29 includes the absorbant pad 15 and the array 17. It should be noted that the invention is not intended to be limited to this particular type of device and other types of device are intended to fall within the scope of the invention. For example, as shown in FIG. 4, in an alternative embodiment, the pump mechanism 20 and the medicament reservoir 12 could be both located in the disposable part 29, and the drive motor 21 may be located in the reusable part 28. In the embodiment shown in FIG. 4, the pump mechanism 20 may be in the form of a peristaltic pump or radial pump. In such an embodiment, a mechanical coupling 38 may be provided between a drive output from the motor, and a drive input to the pump mechanism 20. In a further variant, the device 10 could comprise a single part, which could be either fully disposable or fully reusable.

Figure 5A:
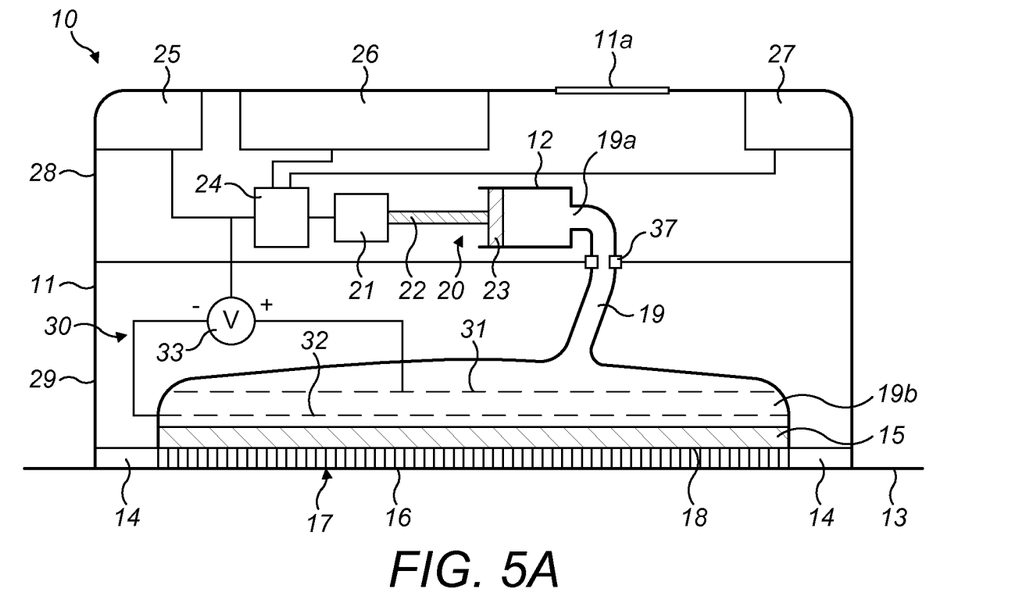
FIG. 5A is a schematic cross-sectional view of a medicament delivery device according to an embodiment.

As shown in FIG. 5A, the device 10 further comprises a system 30 for electrically enhancing the penetration of the medicament into the skin of the patient. In the embodiment shown in FIG. 5A, the system 30 comprises a first electrode or upper electrode 31(anode), a second electrode or lower electrode 32 (cathode), and a DC voltage generator 33 connected to the upper and lower electrodes 31, 32. The upper and lower electrodes 31, 32 are separated by an electrically insulating material to avoid short circuits. The absorbant pad 15 may play the role of such insulating material. Alternatively, for example in an embodiment where the absorbant pad 15 is omitted, an electrically insulating perforated sheet, e.g. in plastic, may be disposed between the upper and lower electrodes 31, 32. In a further alternative, the electrical insulation between the upper and lower electrodes 31, 32 may be created by means of a plurality of insulating balls, e.g. in plastic or covered with a plastic material having electrical insulating properties. The system 30 is configured to generate between the upper and lower electrodes 31, 32 an electric field for driving or accelerating the medicament towards the skin of the patient. Specifically, the system 30 is configured to generate between the upper and lower electrodes 31, 32 pulses of electric current between the upper and lower electrodes 31, 32 for driving or accelerating the medicament towards the skin of the patient.

Figure 5B:
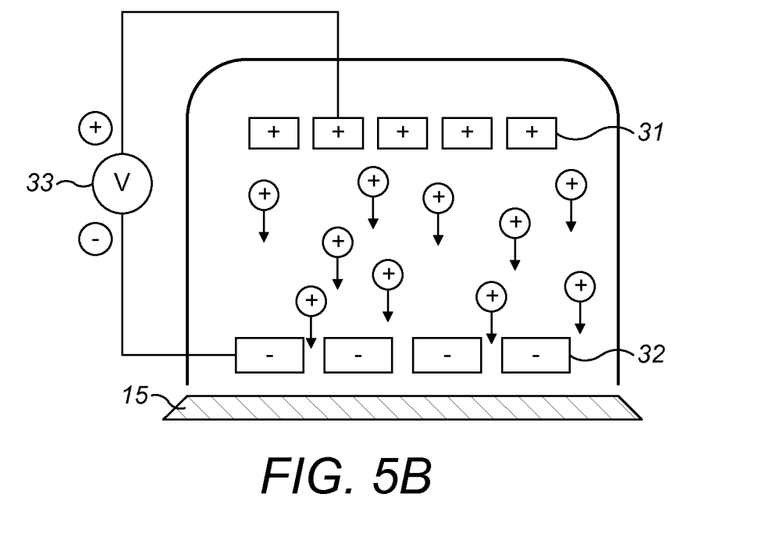
FIG. 5B is a detail of a medicament delivery device according to a variant of the embodiment shown in FIG. 5A.

The upper and lower electrodes 31, 32 are in the form of parallel metallic plates disposed subtantially parallel to each other to form a capacitor. The upper and lower electrodes 31, 32 are respectively disposed upstream and downstream of the absorbant pad 15. Alternatively, as shown in FIG. 5B, the upper and lower electrodes 31, 32 are disposed upstream of the absorbant pad 15. For example, the upper and lower electrodes 31, 32 are disposed in the dispense outlet 19b. The upper and/or lower electrodes 31, 32 are permeable such that, in use, medicament flows through the upper and/or lower electrodes 31, 32 towards the absorbant pad 15. For example, the upper and/or lower electrodes 31, 32 are in the form of a perforated plate or hole mask.

The DC voltage generator 33 is configured to generate a voltage difference between the upper and lower electrodes 31, 32. In the embodiment shown in FIG. 5A, the DC voltage generator 33 is located in the disposable part 29 of the device 10. However, the DC voltage generator 33 could be located at a different location in the device 10, e.g. in the reusable part 28.

The upper electrode 31 and the lower electrode 32 are arranged relative to each other such that the strength of the electric field between the upper and lower electrodes 31, 32 is optimised. The relation between the electric field generated and the distance between the upper and lower electrodes 31, 32 is defined as follows:

$$E = \frac{V}{d}$$

where E is the electric field, V is the voltage differential between the upper and lower electrodes 31, 32, and d is the distance between the upper and lower electrodes 31, 32. Therefore, it is desirable to have a distance d between the upper and lower electrodes 31, 32 as small as possible in order to generate an electric field having a strength as high as possible.

The system 30 is configured to generate high voltage and short duration pulses between the upper electrode 31 and the lower electrode 32. The voltage differential between the upper and lower electrodes 31, 32 preferably ranges around 50 volts. The duration of the pulses is preferably around one or more seconds.

In use, the medicament flows from the reservoir 12 into the manifold 19, towards the dispense outlet 19b and between the upper and lower electrodes 31, 32. The medicament flows between the upper and lower electrodes 31, 32 e.g. by means of a capillary force. The pulsed electric field generated between the upper and lower electrodes 31, 32 accelerates molecules in the medicament, e.g. insulin molecules in the case where the device 10 is an insulin delivery device, or more generally polar molecules that are present in the medicament, towards the lower electrode 32 and towards the skin of the patient. This process, also known as electroporation, ensures that the medicament is optimally transported through the skin of the patient. As shown in FIG. 5B, the electric field generated between the upper and lower electrodes 31, 32 ionizes the molecules of air present between the upper and lower electrodes 31, 32. The ions generated are accelerated by the electric field towards the lower electrode 32. The ions allows to further open the skin pores, thereby further enhancing penetration of medicament through the skin. Ventilation means such as a fan could be provided in the device 10 to further accelerate the medicament towards the patient'skin.

The high voltage, short duration pulses applied to the skin of the patient allow to effectively enhance skin penetration of molecules and water based compounds of the medicament into the skin. For example, the number of transdermal pathways available via electroporation is over 500 times more than the number of transdermal pathways available via iontophoresis. The pulsed electric field generated creates pathways in lipid bilayer membranes of the skin, thereby making the penetration of the medicament through the skin easier. The device 10 therefore allows to increase the permeability of the skin of the patient. Specifically, the device 10 allows to transport through the skin a higher volume of medicament than a conventional transdermal medicament delivery device. The system 30 also allows to transport through the skin molecules of higher molecular weight than with a conventional transdermal medicament delivery device. In particular, the combination of the system 30 and the array 17 of microneedles 16 allows to overcome more easily the skin barrier and therefore to administer the medicament more efficiently than with a conventional medicament delivery device.

Figure 6A:
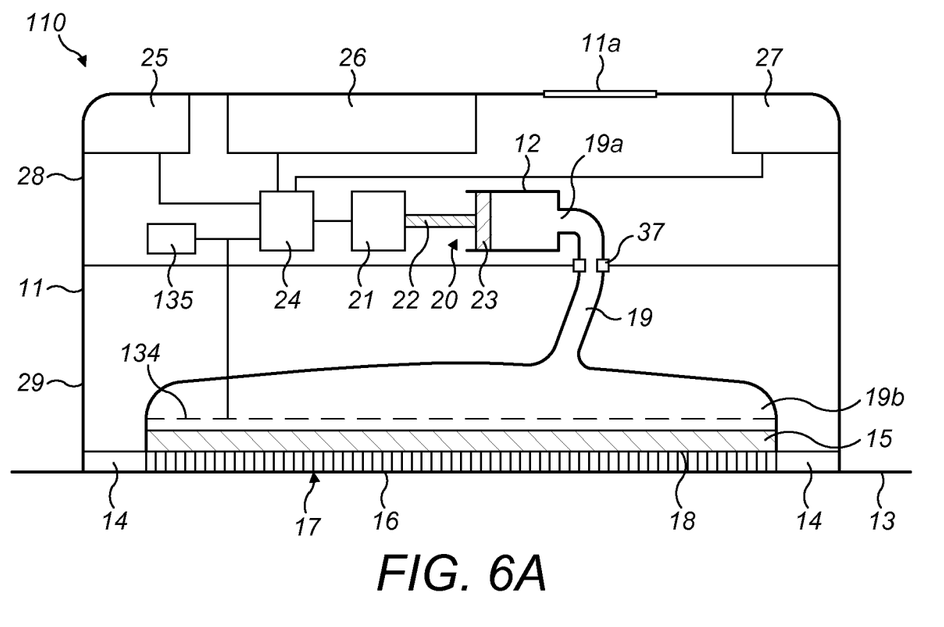
FIG. 6A is a schematic cross-sectional view of a medicament delivery device according to a further embodiment.

A medicament injection device 110 according to a further embodiment is shown in FIG. 6A. The further embodiment corresponds closely to the first embodiment and like reference numerals have been used for like components. Differences in relation to the first embodiment are described below.

The device 110 comprises a heating system 130 for enhancing the penetration of the medicament through the skin of the patient. In the embodiment shown in FIG. 6A, the heating system 130 comprises a heating element 134 configured to heat the skin of the patient. The heating element 134 is permeable such that, in use, medicament flows through the heating element 134 towards the skin of the patient. For example, the heating element 134 is in the form of a perforated foil. In a variant, the heating element 134 is in the form of a coiled resistance. The heating element 134 is preferably electrically insulated. The heating element 134 is disposed at the dispense outlet 19b, upstream of the absorbant pad 15. The heating element 134 is disposed parallel to the absorbant pad 15. Preferably, the heating element 134 extends along a distance greater than half of the length of the absorbant pad 15, so that the absorbant pad 15 is efficiently and uniformly heated.

Figure 6B:
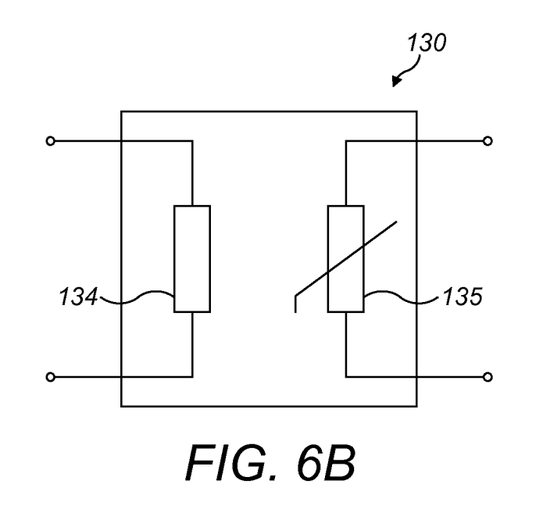
FIG. 6B shows a block diagram of the heating system of the medicament delivery device of FIG. 6A.

The system 130 comprises a heat controller 135 for controlling the temperature of the heating element 134. The heat controller 135 comprises a temperature sensor. The temperature sensor is for example in the form of a NTC thermistor, a PTC thermistor, a semiconductor or a thermocouple working with the Seebeck effect.

In use, the heating system 130 heats the medicament as well as the injection site. The heating allows to increase the blood flow in the body of the patient, proximate the injection site, which enhances the medicament diffusion process. The heating allows to enhance microcirculation in the area of the injection site, thus facilitating medicament transfer into the body of the patient.

In use, the temperature of the heating element 134 should be sufficiently high for enhancing efficiently the medicament diffusion process. However, the temperature should not be too high to avoid sweating of the skin, which could decrease the efficiency of the medicament absorption and cause detachment of the device 110 from the skin. In use, the temperature of the heating element 134 is preferably around five degrees higher than the temperature of the skin of the patient. A temperature sensor may be provided in the device 110 to maintain the heating element 134 at such temperature. Alternatively, a sensor may be provided in the device 110 to measure the temperature of the room in which the medicament delivery is performed, such that the temperature of the heating element 134 is maintained at a higher value than the temperature of the room, e.g. around five degrees higher than the temperature of the room.

Figure 7:
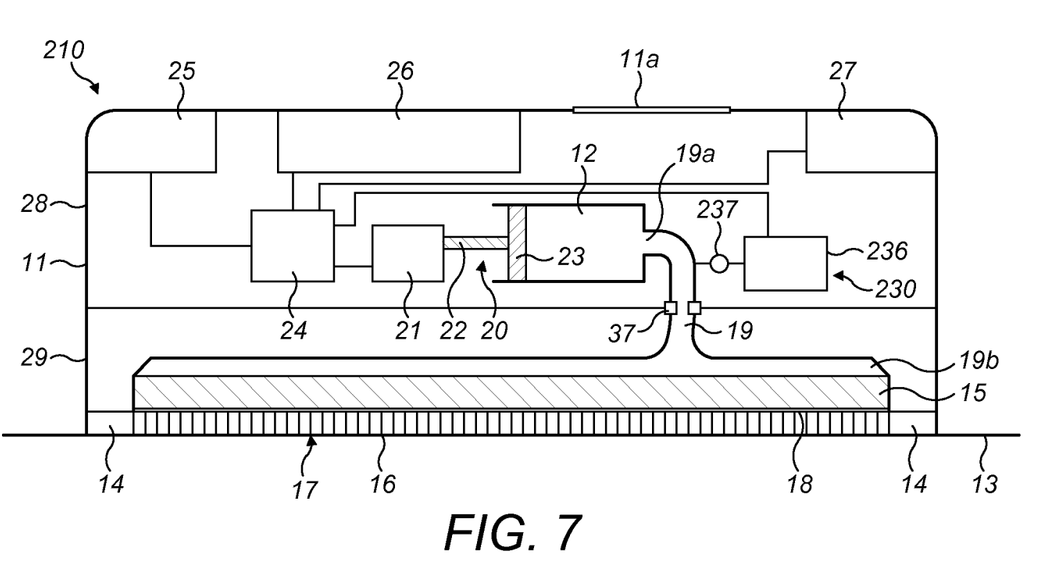
FIG. 7 is a schematic cross-sectional view of a medicament delivery device according to a still further embodiment.

A medicament injection device 210 according to a further embodiment is shown in FIG. 7. The further embodiment corresponds closely to the first embodiment and like reference numerals have been used for like components. Differences in relation to the first embodiment are described below.

The device 210 comprises a system 230 for chemically enhancing the penetration of the medicament into the skin of the patient. In the embodiment shown in FIG. 7, the system 230 is configured to deliver a support agent or pore opener or chemical penetration enhancer to the patient. As shown in FIG. 7, the system 230 comprises a mechanism for mixing the chemical penetration enhancer to the medicament prior to the medicament delivery into the skin of the patient. The mechanism comprises a reservoir 236 for storing the chemical penetration enhancer and a pump 237 for pumping the chemical penetration enhancer into the manifold 19 where the chemical penetration enhancer contacts the medicament.

The chemical penetration enhancer is, for example, Dimethyl sulfoxide (DMSO). Mixing the medicament with DMSO allows to efficiently improve the medicament absorption through the skin. In a variant, alcohol such as ethanol can be added to the medicament prior to the medicament delivery. In a further variant, a solution may be added to the medicament to lower the pH value of the medicament such that the medicament has a pH lower than the pH of the skin of the patient. For example, a saline solution may be used. The resulting pH gradient between the medicament and the skin results in a chemical force which drives the medicament through the skin and ensures that the medicament is efficiently absorbed. In further alternatives, other substances, such as a fat subtance, or urea, can also be added to the medicament to chemically increase the permeability of the skin. The chemical penetration enhancer is chosen depending on the medicament to be delivered.

In one embodiment, the medicament is mixed with an agent to ensure that the salt concentration in the skin of the patient and body is greater than the salt concentration in the liquid medicament, so that the osmotic pressure created by the gradient of salt concentration between the skin of the patient and the medicament draws the medicament towards the skin of the patient.

Alternatively, or additionally, the chemical penetration enhancer may be provided at the bottom surface or skin attachement side of the device 210. The bottom surface may for example comprise a layer of chemical penetration enhancer. In one embodiment, the bottom surface includes a layer of water-based substance. Increasing the amount of water at the skin surface allows to moisturize the skin surface and to consequently open skin pores at the injection site, thereby enhancing the permeability of the skin. Alternatively, a layer of oil-based substance may be provided at the bottom surface of the device 210.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The term "drug delivery device" shall encompass any type of device or system configured to dispense a drug or medicament into a human or animal body. Without limitation, a drug delivery device may be an injection device (e.g., pen injector, auto injector, large-volume device, pump, perfusion system, or other device configured for intraocular, subcutaneous, intramuscular, or intravascular delivery), skin patch (e.g., osmotic, chemical), inhaler (e.g., nasal or pulmonary), an implantable device (e.g., drug- or API-coated stent, capsule), or a feeding system for the gastro-intestinal tract.

The drug or medicament may be contained in a primary package or "drug container" adapted for use with a drug delivery device. The drug container may be, e.g., a cartridge, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refer to any substance which is sufficiently structurally similar to the original substance so as to have substantially similar functionality or activity (e.g., therapeutic effectiveness). In particular, the term "analogue" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyhepta¬decanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigens. The antibody can be polyclonal, monoclonal, recombinant, chimeric, de-immunized or humanized, fully human, non-human, (e.g., murine), or single chain antibody. In some embodiments, the antibody has effector function and can fix a complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit, which encompass such modifications and any and all equivalents thereof.

The invention claimed is:

1. A medicament delivery device comprising:
   at least one microneedle for delivering a medicament to a patient; and
   a system configured to enhance penetration of the medicament into skin of a patient;
   wherein the system comprises a first electrode, a second electrode, and a power supply connected to the first and second electrodes, the system being configured to generate an electric field between the first and second electrodes, the first and second electrodes being arranged such that, in use, the electric field generated between the first and second electrodes drives the medicament towards the skin of the patient, and
   wherein the second electrode is permeable to allow the medicament driven by the electric field to flow through the second electrode towards the skin of the patient.

2. The medicament delivery device according to claim 1, wherein the system is configured to generate a pulsed electric field between the first and second electrodes.

3. The medicament delivery device according to claim 1, wherein the system comprises a heating element configured to heat the skin of the patient.

4. The medicament delivery device according to claim 3, wherein the heating element is permeable to allow the medicament to flow through the heating element towards the skin of the patient.

5. The medicament delivery device according to claim 3, wherein the system comprises a heat controller for controlling the heating element.

6. The medicament delivery device according to claim 1, wherein the system is configured to deliver a chemical penetration enhancer into the skin of the patient.

7. The medicament delivery device according to claim 6, wherein the system comprises a mechanism for mixing the chemical penetration enhancer with the medicament prior to delivery of the medicament into the skin of the patient.

8. The medicament delivery device according to claim 1, comprising a porous membrane arranged adjacent to the at least one microneedle, the porous membrane being configured to retain the medicament.

9. The medicament delivery device according to claim 1, comprising a medicament pump mechanism for pumping the medicament towards the at least one microneedle.

10. The medicament delivery device according to claim 9, comprising a reusable part and a disposable part, and wherein the medicament pump mechanism is located in the disposable part.

11. The medicament delivery device according to claim 1, comprising a plurality of microneedles.

12. The medicament delivery device according to claim 1, comprising a cartridge containing the medicament.

13. The medicament delivery device according to claim 1, wherein the medicament delivery device is an insulin delivery device.

* * * * *